(12) United States Patent
Abdou

(10) Patent No.: US 8,273,005 B2
(45) Date of Patent: Sep. 25, 2012

(54) TREATMENT OF PAIN, NEUROLOGICAL DYSFUNCTION AND NEOPLASMS USING RADIATION DELIVERY CATHETERS

(76) Inventor: Samy Abdou, San Diego, CA (US)

( * ) Notice: Subject to any disclaimer, the term of this patent is extended or adjusted under 35 U.S.C. 154(b) by 1350 days.

(21) Appl. No.: 11/670,927

(22) Filed: Feb. 2, 2007

(65) Prior Publication Data

US 2007/0185367 A1  Aug. 9, 2007

Related U.S. Application Data

(60) Provisional application No. 60/764,456, filed on Feb. 2, 2006, provisional application No. 60/815,194, filed on Jun. 19, 2006.

(51) Int. Cl.
*A61N 5/00* (2006.01)
(52) U.S. Cl. .......................... 600/3; 604/500
(58) Field of Classification Search ............... 600/1–8; 128/897–898
See application file for complete search history.

(56) References Cited

U.S. PATENT DOCUMENTS

| | | | |
|---|---|---|---|
| 6,261,291 B1 | 7/2001 | Talaber et al. | |
| 6,638,276 B2 | 10/2003 | Sharkey et al. | |
| 6,683,690 B1 | 1/2004 | Tobias | |
| 6,726,685 B2 | 4/2004 | To et al. | |
| 6,733,496 B2 | 5/2004 | Sharkey et al. | |
| 6,790,210 B1 | 9/2004 | Cragg et al. | |
| 6,832,997 B2 | 12/2004 | Uchida et al. | |
| 6,837,884 B2 | 1/2005 | Woloszko | |
| 6,896,675 B2 | 5/2005 | Leung et al. | |
| 6,926,658 B2 | 8/2005 | Farnan | |
| 6,929,640 B1 | 8/2005 | Underwood et al. | |
| 6,980,862 B2 | 12/2005 | Fredricks et al. | |
| 6,994,688 B2 | 2/2006 | Brauckman et al. | |
| 6,997,941 B2 | 2/2006 | Sharkey et al. | |
| 7,011,619 B1 | 3/2006 | Lewis et al. | |
| 7,014,633 B2 | 3/2006 | Cragg | |
| 7,025,716 B1 | 4/2006 | Meloul et al. | |
| 7,094,258 B2 | 8/2006 | Lambrecht et al. | |
| 7,122,629 B2 | 10/2006 | Bejanin et al. | |
| 7,144,397 B2 | 12/2006 | Lambrecht et al. | |
| 2001/0056219 A1* | 12/2001 | Brauckman et al. | 600/3 |
| 2002/0019626 A1 | 2/2002 | Sharkey et al. | |
| 2003/0233136 A1* | 12/2003 | Williams et al. | 607/50 |
| 2004/0111136 A1 | 6/2004 | Sharkey et al. | |
| 2004/0127963 A1 | 7/2004 | Uchida et al. | |
| 2004/0193151 A1 | 9/2004 | To et al. | |
| 2005/0177209 A1 | 8/2005 | Leung et al. | |
| 2005/0177210 A1 | 8/2005 | Leung et al. | |
| 2005/0177211 A1 | 8/2005 | Leung et al. | |
| 2006/0200121 A1* | 9/2006 | Mowery | 606/41 |

* cited by examiner

*Primary Examiner* — John Lacyk
*Assistant Examiner* — Carrie R Dorna
(74) *Attorney, Agent, or Firm* — Gazdzinski & Associates, PC (57) ABSTRACT

A catheter-based radiation delivery system is adapted to treat pain, nervous system injury, and select neoplasms. A source of pain is identified within soft tissues of an individual or an animal. A needle or catheter is then used to deliver radiation to the source of pain.

10 Claims, 8 Drawing Sheets

TREATMENT OF PAIN, NEUROLOGICAL DYSFUNCTION AND NEOPLASMS USING RADIATION DELIVERY CATHETERS

REFERENCE TO PRIORITY DOCUMENT

This application claims priority of the following co-pending U.S. Provisional Patent Applications: (1) U.S. Provisional Patent Application Ser. No. 60/764,456, filed Feb. 2, 2006; and (2) U.S. Provisional Patent Application Ser. No. 60/815,194, filed Jun. 19, 2006. Priority of the aforementioned filing dates is hereby claimed and the disclosure of the Provisional Patent Applications are hereby incorporated by reference in their entirety.

BACKGROUND

The present disclosure is related to medical procedures for the treatment of pain, spinal disease, neurologic dysfunction and neoplasms.

Chronic pain is one of the most common and disabling disorders afflicting humanity. In the United States alone, more than 50 million individuals live with the burden of chronic pain and, for at least two thirds of these Americans, the pain has been present for more than five years. The economic costs of chronic pain to both the sufferer and society are substantial. Recent studies show that more than 35 million Americans will miss work each year because of pain and at least 80 million Americans with chronic pain live with significant limitations in functional capability and quality of life.

Spinal cord injury and other insults to the nervous system—such as stroke, traumatic brain injury, traumatic disruption of the peripheral nerves, and the like—are additional causes of devastating disability. In addition to producing chronic pain, these afflictions can permanently disable otherwise productive members of society. While the initial injury disrupts the functional status of the nervous system, it is the formation of scar tissue at the site of injury that greatly retards neuronal healing and turns the initial functional deficit into a permanent neurological disability.

The limited capacity of human organ systems to repair and restore function after injury is well known. Unlike some species that are capable of complete organ or limb regeneration, human organ systems respond to injury by forming scar tissue. With the exception of bone, all human organ systems will produce varying amounts of scar tissue in the healing process. Since scar formation replaces the native functional tissue with non-functional scar, the healing process necessarily produces a repaired organ system with diminished capability.

In general, the regenerative capability of an organ system is inversely proportional to its level of specialization and complexity. As the most specialized organ system, the nervous system has a limited capacity to regenerate and recoup function after injury. This is especially evident in spinal cord injury. Patients who suffer significant spinal cord trauma may not regain any meaningful function. Recent studies into the cellular events that occur after nervous system injury have demonstrated that scar formation is a major limiting factor in recovery. That is, the forming scar limits the extent of neuronal regeneration and inhibits the re-establishment of normal communication between nerve cells. Likewise, the inhibition of scar formation has been shown to increase functional recovery after injury.

Radiation is a known inhibitor of the healing process and scar formation. Because of the negative effect on healing, the exposure of injured tissues to radiation is generally undesirable and contra-indicated. Irradiation of injured neural tissue can paradoxically improve neurological recovery by limiting the extent of scar formation. However, a radiation source external to the body is indiscriminate and cannot be effectively used to selectively radiate an injury site while sparing the surrounding tissues.

This is an inherent limitation of the use of external beam radiation sources that cannot be readily circumvented. In view of the foregoing, there is a need for improved systems and methods for treating injury, including neurological injury.

SUMMARY

The systems and methods provided herein satisfy this as well as other needs. The systems and methods provided herein allow for the selective and minimally invasive irradiation of tissues. Also provided are improved systems and methods for treating neurological injury. Disclosed is a catheter-based radiation delivery system to treat pain, nervous system injury, and select neoplasms. In one embodiment, a source of pain is identified within soft tissues of an individual or an animal. A needle and/or catheter is passed into the soft tissue and aimed at the purported site of pain. A second needle is passed through the central lumen of the first needle/catheter. A local anesthetic of defined dose and volume is injected at the site of pain to confirm the location of the pain generator. An alleviation of pain by the anesthetic is considered a positive result and indicates localization of the tissue/nerve fibers that produce the pain. The inner needle is withdrawn and a catheter capable of delivering a radiation dose is passed into the site of the pain generator through the outer needle/catheter. The radiation dose is delivered and all devices are withdrawn.

In another embodiment, a balloon catheter is delivered to the site of the pain generator and the balloon is then filled with a radiation source so as to deliver a radiation dose to the site. The procedure can be performed as described or, alternatively, the radiation dose can be delivered directly to the tissue without the initial trial of a local anesthetic.

In another embodiment, a spinal nerve is localized as the pain generator using an anesthetic injection as previously described. The nerve is then irradiated using a catheter-based radiation delivery system in a manner similar to that described above. In another embodiment, a painful joint can be similarly irradiated. In addition, a symptomatic spinal disc can be percutaneously entered using any one of the many known approaches for accessing the disc space. Radiation is then delivered to the inner aspect of the disc and the annulus fibrosis using a catheter-based radiation delivery system. Preferably, the pain-generating character of the disc is confirmed using the above-mentioned local anesthetic injection method prior to disc space irradiation.

In another embodiment, a site of nervous system injury is irradiated using a catheter-based radiation delivery system. In the spinal cord, for example, the radiation delivery can be performed at the time of operation for another purpose, such as for the stabilization of the spinal column, or, alternatively, the catheter can be percutaneously introduced into the subarachnoid space and then floated within the cerebro-spinal fluid (CSF) to the site of injury.

In another embodiment, a catheter-based radiation delivery system is placed into the site of a neoplasm and used to directly irradiate the lesion. The catheter can be also used to deliver other agents to the tumor that would potentiate the anti-neoplastic effects of radiation. These agents are well known and would include chemotherapeutic drugs, agents that alter the local tissue oxygen tension or influence free radical formation/breakdown, photo-therapeutic agents, and the like.

Other features and advantages will be apparent from the following description of various methods and will illustrate, by way of example, the principles of the disclosed invention.

DETAILED DESCRIPTION

Provided herein is a catheter-based radiation delivery system to treat pain, nervous system injury, and neoplasms. The systems and methods provided herein allow for the selective and minimally invasive irradiation of tissues.

In spinal cord injury, for example, laboratory data suggest that irradiation of the injury site can increase the functional recovery of the injured animal. While a radiation source external to the body can be used to irradiate the spinal cord, this form of treatment is indiscriminate and cannot be effectively used to selectively radiate the site of spinal cord injury while sparing the surrounding tissues. Since spinal cord injury is often a result of spinal fracture and/or dislocation, it is highly advantageous to limit the radiation exposure to the injured spinal cord while shielding the surrounding bone and soft tissues. Radiation of the latter structures would have a negative effect on the healing capabilities of those injured tissues. A method for the selective and minimally invasive irradiation of neural tissue is highly advantageous and desirable.

The application of radiation energy to the intact nervous system is also known to significantly modulate nerve conduction and function. Since pain perception is a direct result of pain nerve fiber discharge and subsequent signal processing within the central nervous system, it is possible to use radiation to lessen or cure chronic pain. In current medical practice, for example, irradiation of the nerve that provides facial sensation is commonly used to successfully treat the excruciating facial pain of trigeminal neuralgia. In this condition, the radiation is delivered to the nerve from an external source and aimed using known cranial anatomy. While this technique can be used with a nerve that has a constant and well-defined anatomical course, it is far less applicable in the great majority of nerves that are more variable in position.

A significant proportion of chronic pain is caused by disorders of the spinal column, spinal nerves, and/or peripheral nerves. Efforts to use radiation to treat pain syndromes that are caused by spinal and/or peripheral nerve pathology have been significantly hampered by the inability to accurately target these structures without the unwanted irradiation of the adjacent spinal cord and other critical tissues. This is an inherent limitation of the use of external beam radiation sources that cannot be readily circumvented. Once again, it is clear that a method for the selective and minimally invasive irradiation of tissues is needed. It can provide a desirable and highly advantageous way of treating chronic pain.

In an unrelated medical development, cardiologists employ a catheter-based system to deliver radiation within blood vessels. These devices are used to irradiate intra-vascular stents in hopes of decreasing the rate of restenosis within these vascular conduits. U.S. Pat. Nos. 7,122,629; 7,025,716; 7,011,619; 6,994,688; 6,926,658; 6,683,690; 6,261,291 and others disclose systems and methods of catheter-based radiation delivery devices. However, there are no descriptions in the prior art or within the published medical literature of these device being used to treat pain, to improve functional recovery after neurological injury, or to treat select neoplasms.

Figure 1:
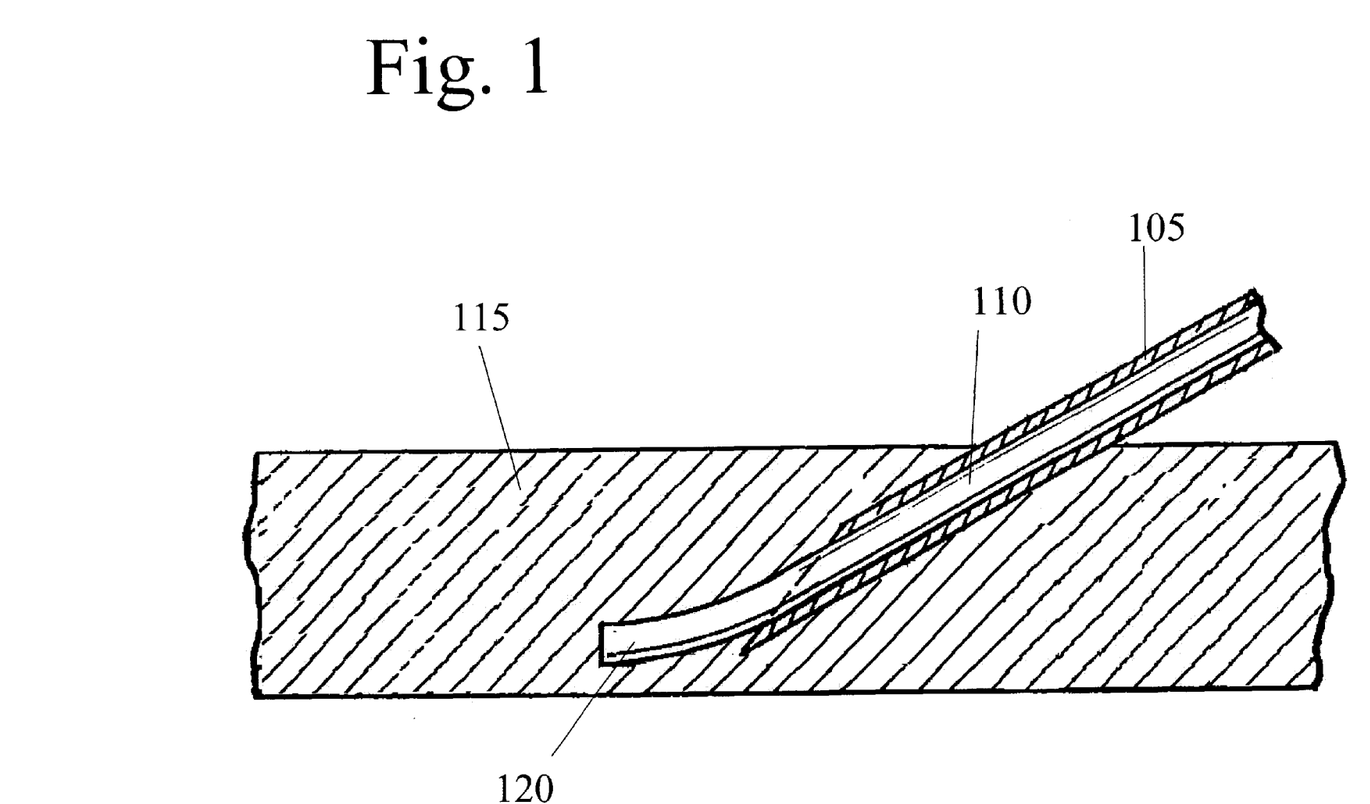
FIG. 1 shows a first embodiment of the catheter-based radiation delivery system.

Disclosed is a catheter-based radiation delivery system to treat pain, nervous system injury, scar formation, and select neoplasms. FIG. 1 shows a first embodiment of the catheter-based radiation delivery system. A needle device 105 with a central bore 110 is shown inserted into tissue 115 at a site of pain. The tissue 115 is represented schematically in FIG. 1 for clarity of illustration. The needle device 105 can be used to target a particular peripheral nerve within the painful tissue or it can be simply inserted at the purported site of the pain generator without specifically targeting a defined nerve.

With reference still to FIG. 1, the central bore 110 is sized to receive a catheter 120 therethrough. The catheter 120 is adapted to deliver a radiation dose to the tissue. In this regard, the catheter 120 can be coupled to a radioactive source such as at a proximal end of the catheter 120. Alternately, the catheter 120 can be filled internally with a radioactive material. The catheter 120 can also be at least partially formed of a radioactive material. The catheter 120 is shown such that its distal end emerges out of the distal end of the needle device 115. The distal end of the catheter 120 is positioned to deliver a dose of radiation to a location where pain is generated. The location of the pain generator can be confirmed by locally injecting an anesthetic agent prior to tissue irradiation. A local anesthetic of defined dose and volume is injected at the site of pain to confirm the location of the pain generator. An alleviation of pain by the anesthetic is considered a positive result and indicates localization of the tissue/nerve fibers that produce the pain.

A catheter can be adapted to deliver radiation using any of a variety of methods and devices. The radioactive source can be bonded and/or chemically absorbed onto the inner and/or outer aspect of the catheter or onto any of the catheter components. The radioactive source can be further positioned or circulated through the catheter body or immobilized within it as gel, elastomer, or other deformable materials. The radiation can be alpha radiation, beta radiation, or gamma radiation. A balloon filled with a radiation source can be alternatively delivered to the target tissue through a non-radioactive catheter port. U.S. Pat. Nos. 7,122,629; 7,025,716; 7,011, 619; 6,994,688; 6,926,658; 6,683,690; 6,261,291, for example, illustrate multiple methods for the adaptation of catheters to deliver a radiation dose. The foregoing patents are incorporated herein by reference in their entirety.

Figure 2:
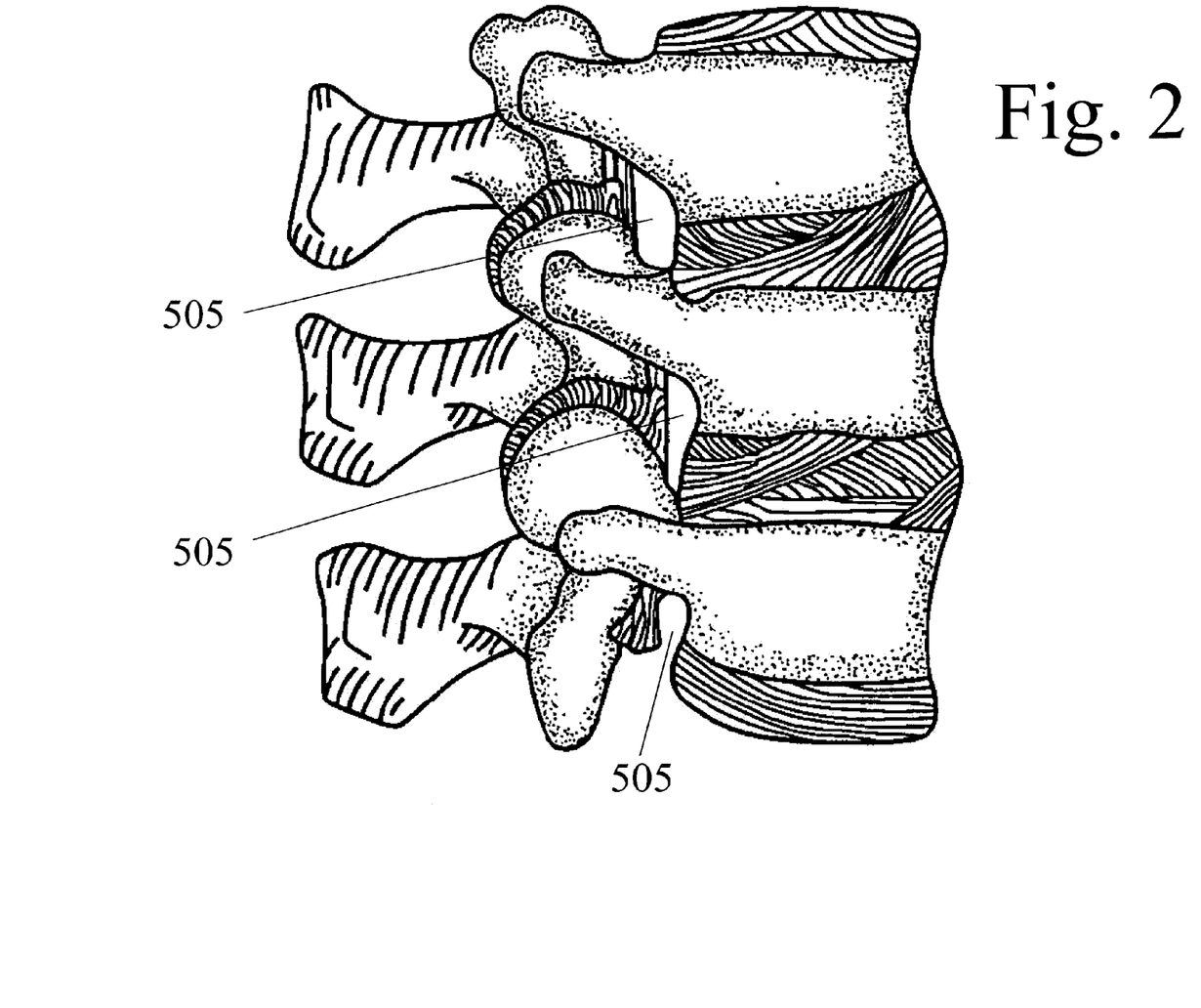
FIG. 2 shows a lateral view of a portion of a human spine with three vertebrae divided by intervertebral discs.
Figure 3:
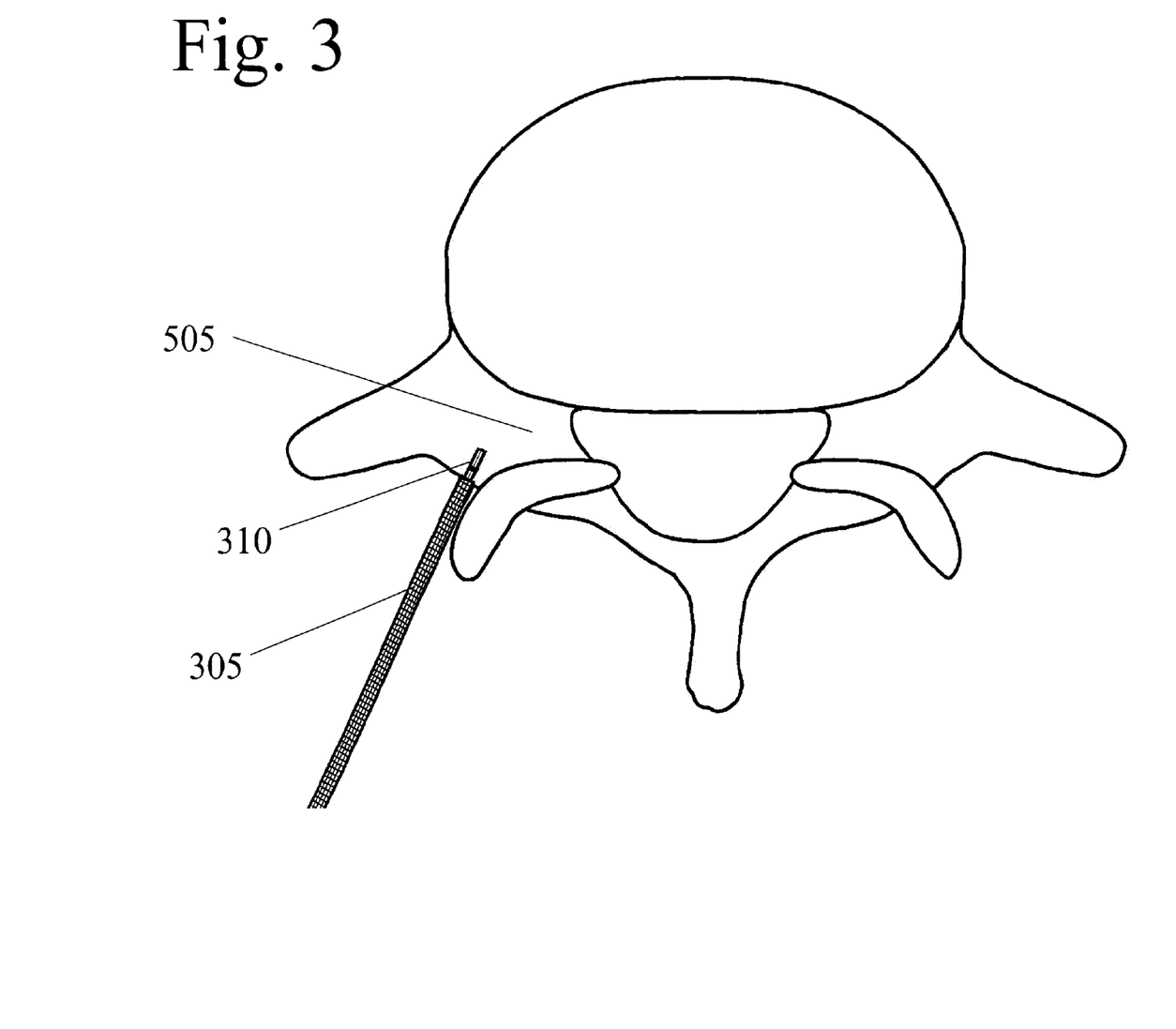
FIG. 3 shows a cross-sectional view of a vertebra along a horizontal plane.

In another embodiment, a needle with a central bore adapted to accept an insertable catheter is percutaneously placed adjacent to a spinal nerve where the nerve exits the spinal column. Spinal nerves predictably exit the spinal column through their respective neural foramen and can be consistently localized at that site. FIG. 2 shows a lateral view of a portion of a human spine with three vertebrae divided by intervertebral discs. The neural foramen 505 is shown in FIG. 2. FIG. 3 shows a cross-sectional view of a vertebra along a horizontal plane. A needle 305 and a radiation delivery catheter 310 are shown percutaneously placed such that a distal region of the catheter 310 is at or near the nerve exit site.

The percutaneous needle localization of spinal nerves is a well-known technique in medical practice and is amply described in the text "Image-guided Spine Intervention" by Douglas Fenton and Leo Czervionke, 2003. The text is hereby incorporated by reference in its entirety. The exiting nerve's involvement in the pain condition can be verified by the local administration of an anesthetic agent as described above. After alleviation of the pain is confirmed, the nerve is irradiated using the catheter-based radiation delivery, such as device shown in FIG. 3. The efficacy of nerve irradiation in the amelioration of pain has been well demonstrated. Advantageously, radiation appears to preferentially inhibit the function of the smaller nerve fibers involved in pain transmission while selectively sparing the larger fibers responsible for muscle function and locomotion.

Low back pain is a leading cause of chronic pain and degenerative disc disease is one of the major causes of low back pain. It is known that, with degeneration, multiple tears and fissures develop within the annulus fibrosis that surrounds the inter-vertebral disc. With healing of these tears, nerve fibers that signal pain grow into and become trapped within the substances of the degenerating inter-vertebral disc. Subsequent loading of the degenerated disc activates the trapped nerve fibers and produces excruciating back pain.

Multiple devices and methods have been developed to treat low back pain. Methods and devices described in U.S. Pat. Nos. 6,980,862; 6,929,640; 6,896,675 (which are all incorporated herein by reference) attempt to apply electrical, thermal or other forms of non-radioactive energy sources to the disc space in hopes of destroying the aberrant nerve fibers that relay pain to the nervous system. Unfortunately, multiple patient trials have shown little or no significant clinical benefit from this treatment strategy. Further, laboratory studies have shown that electrical and thermal energies applied to the disc space have a very limited effect on the aberrant nerve fibers or the surrounding disc tissue. In contrast, radiation is a much more potent modulator of nerve fiber activity.

Figure 4:
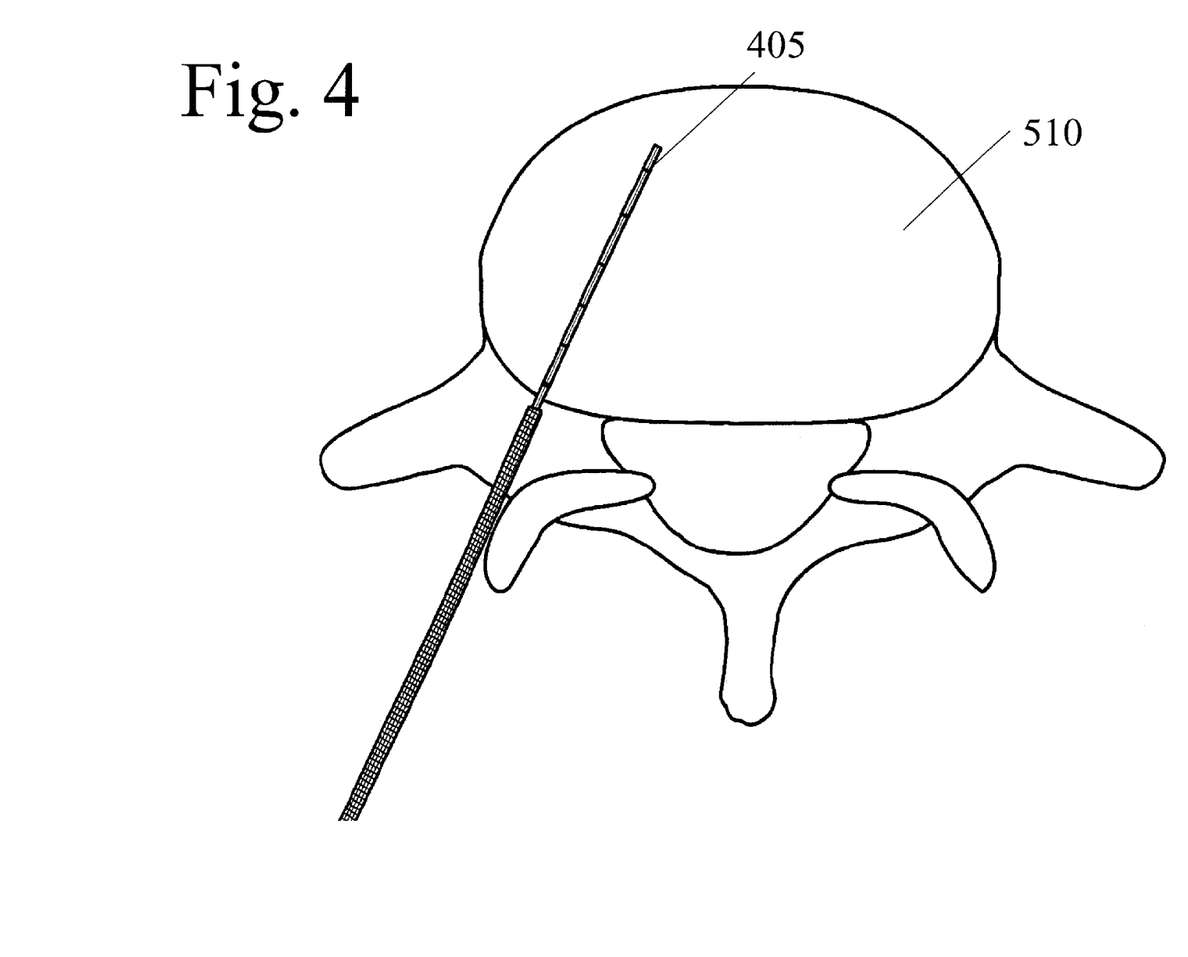
FIGS. 4 and 5 show cross-sectional views of a vertebra along a horizontal plane with a radiation delivery catheter percutaneously positioned within a disc space.
Figure 5:
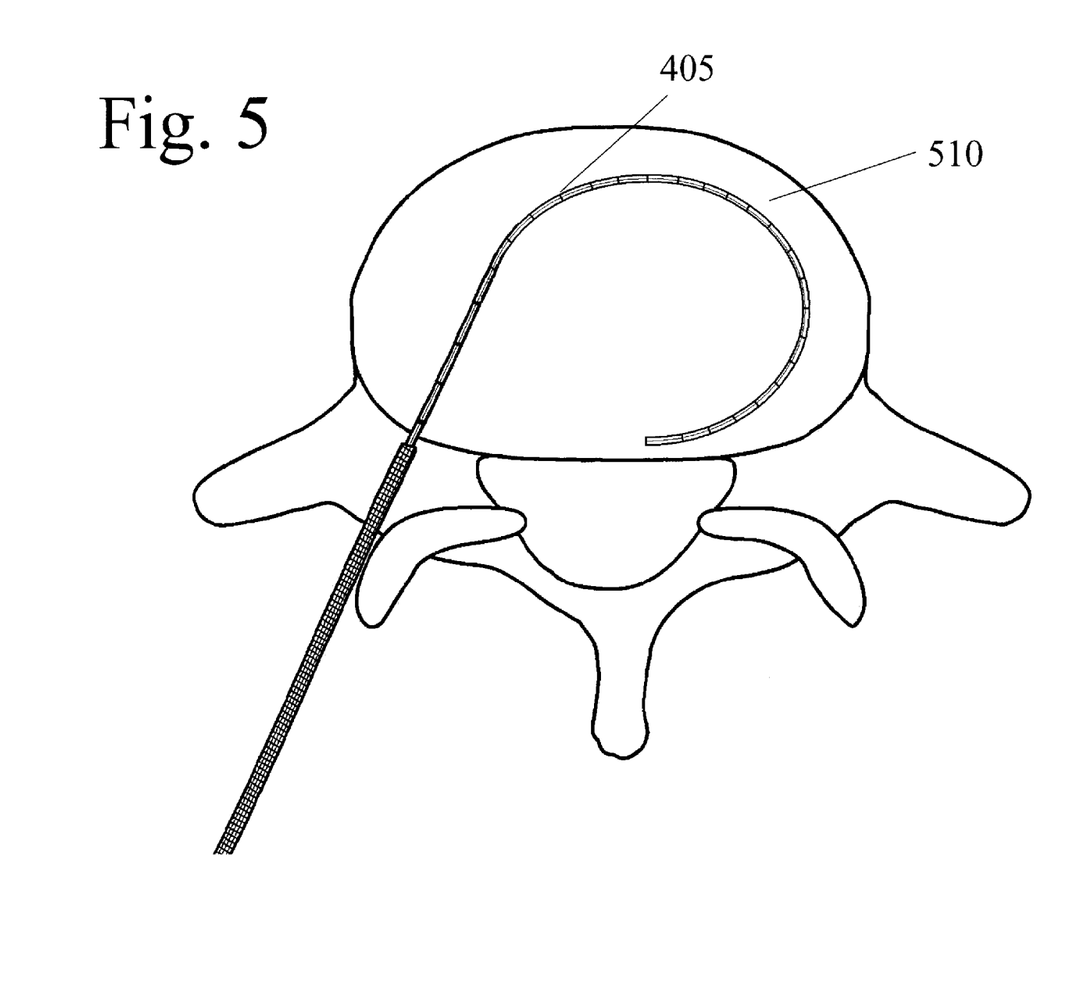

FIGS. 4 and 5 show cross-sectional views of a vertebra along a horizontal plane with a radiation delivery catheter percutaneously positioned within a disc space. The catheter is adapted to access a disc space between two vertebral bodies. In the embodiment of FIG. 4, a substantially straight catheter 405 comprised of an elongated body is positioned within the disc space 510. The catheter 405 is adapted to deliver radiation into the disc space. In the embodiment of FIG. 5, the catheter 405 is contoured to pass along a curvilinear pathway adjacent to the annulus fibrosis. While a straight catheter can be used to deliver the radiation dose, the curvilinear path can deliver the radiation dose more directly to the annulus fibrosis. Strategies for accessing the disc space are described in the aforementioned text by Fenton and Czervionke. In addition, U.S. Patent Application Publication Nos. 20050177211, 20050177210, 20050177209, 20040193151, 20040127963, 20040111136, 20020019626, U.S. Pat. Nos. 7,144,397; 7,094,258; 7,014,633; 6,997,941; 6,929,640; 6,896,675; 6,837,884; 6,832,997; 6,790,210; 6,733,496; 6,726,685; 6,638,276 describe approaches to the disc space. The aforementioned patent publications and patents are incorporated herein by reference.

In an additional embodiment, the catheter is at least partially manufactured from a shape memory alloy and/or polymer. A catheter that is at least partially made from a shape-memory alloy and/or polymer is used to enter the disc space in a first configuration and then transition to a second configuration in response to thermal energy, electric energy, magnetic energy, and the like. As an example, the catheter can be introduced into the disc space in a substantially linear configuration such as shown in FIG. 4. The device then transitions into a different shape, such as a curvilinear configuration as shown in FIG. 5. The device comprising the shape-memory materials can be the radiation delivery catheter itself or an outer non-radioactive introducer device through which the radiation delivery catheter is delivered.

Alternatively, an introducer device that is at least partially made from a shape-memory material can be passed into the disc space. A radiation delivery catheter with an inner bore is then advanced atop the shape memory introducer device and into the disc space. The introducer device can be a needle that is placed directly into the disc space or a guide wire that is placed into the disc through the central bore of a needle device. Once appropriately positioned within the disc, the shape memory device is then changed in configuration.

Shape memory materials plastically deform from a first configuration into a second configuration and then return to the first "memorized" configuration in response to a stimulus. In one type of shape memory material, the stimulus is a temperature change. This feature is an intrinsic property of the material used and the temperature at which the configuration change occurs can be manipulated by varying the elemental composition of the material. The ability of the material to reversibly change shape is secondary to a temperature-dependant phase transformation so that the material essentially exists in either an austenitic state or a martensitic state depending on temperature. Shape-memory materials include a number of shape-memory alloys and shape-memory polymers. The former include a variety of alloys of known metals such as, for example, nickel and titanium, copper and zinc as well as copper, aluminum and nickel. Shape memory polymers have also been described and usually consist of a plastic polymer with two or more components that have different thermal characteristics. These components include, for example, oligo (e-caprolactone) diol and oligo (p-dioxanone) diol. Additional materials exist that reversibly alter shape in reaction to stress, pH, moisture and magnetic and electrical fields. While shape memory materials that transition between configurations with any of these stimuli can be used, shape memory alloys that respond to temperature change are particularly suitable for this application.

Figure 6:
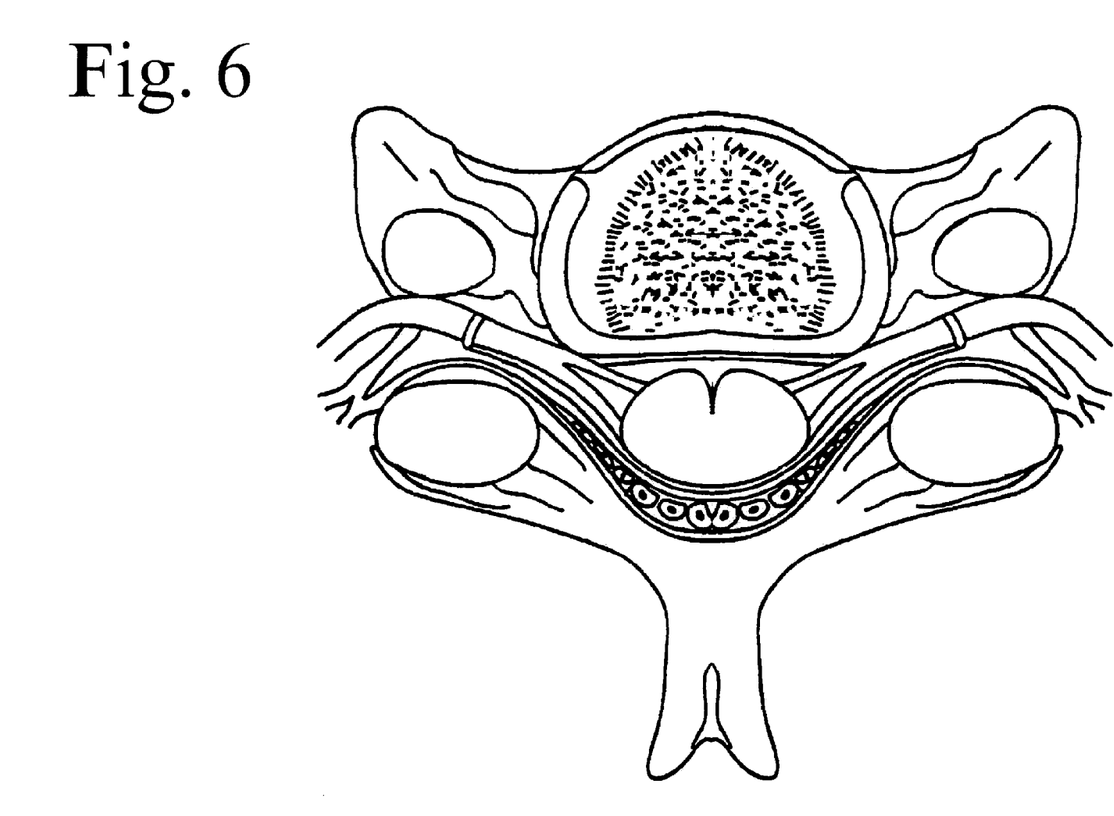
FIG. 6 shows a sectional view of the cervical spine in a horizontal plane.
Figure 7:
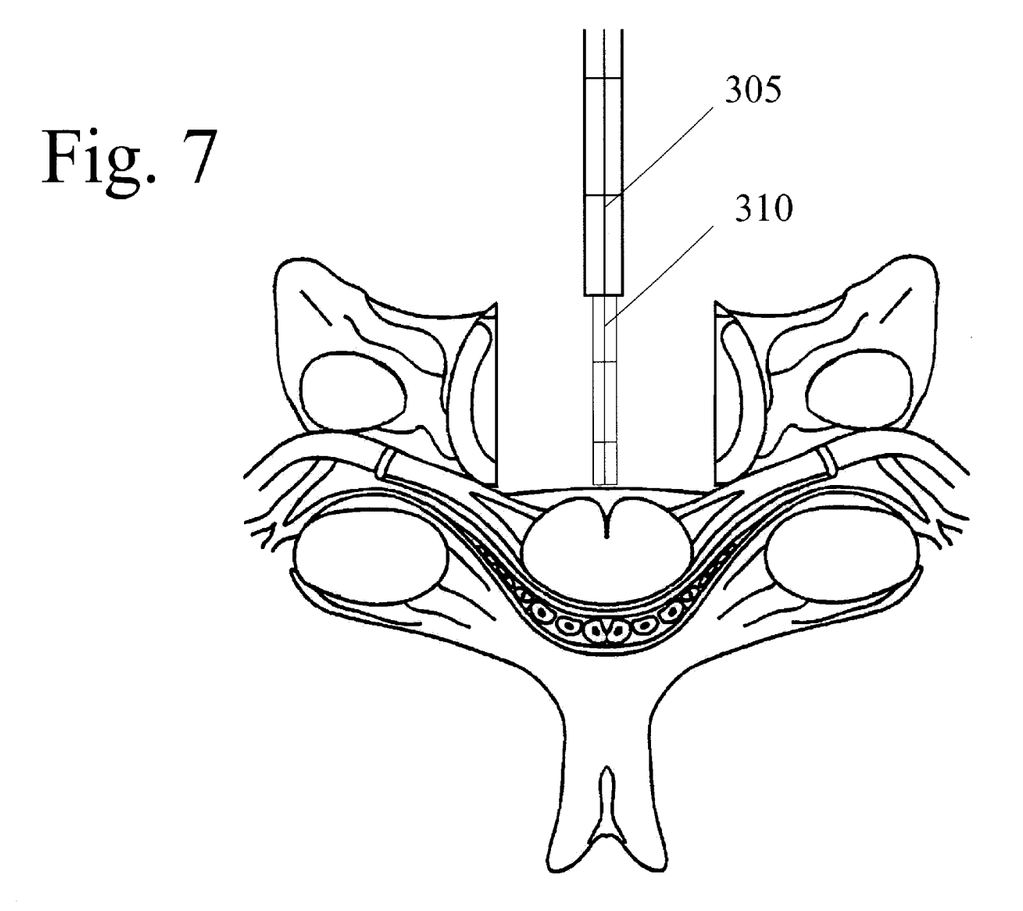
FIG. 7 shows a sectional view of the cervical spine wherein a fractured vertebral body has been surgically removed to achieve decompression of the spinal cord.

FIG. 6 shows a sectional view of the cervical spine in a horizontal plane. Spinal cord injury is most commonly the result of spinal fracture and/or vertebral dislocation. Many of the patients that suffer spinal cord injury will require urgent surgical decompression of the spinal cord and stabilization of the fractured and/or dislocated spinal vertebra. FIG. 7 shows a sectional view of the cervical spine wherein a fractured vertebral body has been surgically removed to achieve decompression of the spinal cord. The spinal cord is already exposed during these surgical operations such that direct and selective irradiation of the injured spinal cord segment can be readily performed.

With reference to FIG. 7, the catheter-based radiation delivery system is shown positioned next to the spinal cord. The radiation delivery catheter 310 extends outwardly from a delivery needle 305. In patients where surgical intervention is not required, the catheter 310 can be passed into the subarachnoid space and then advanced within the spinal fluid compartment to the area of spinal cord injury. The catheter 310 is then used to irradiate the injured tissue. Likewise, the catheter-based radiation delivery system can be used to irradiate other sites of nervous system injury.

Figure 8:
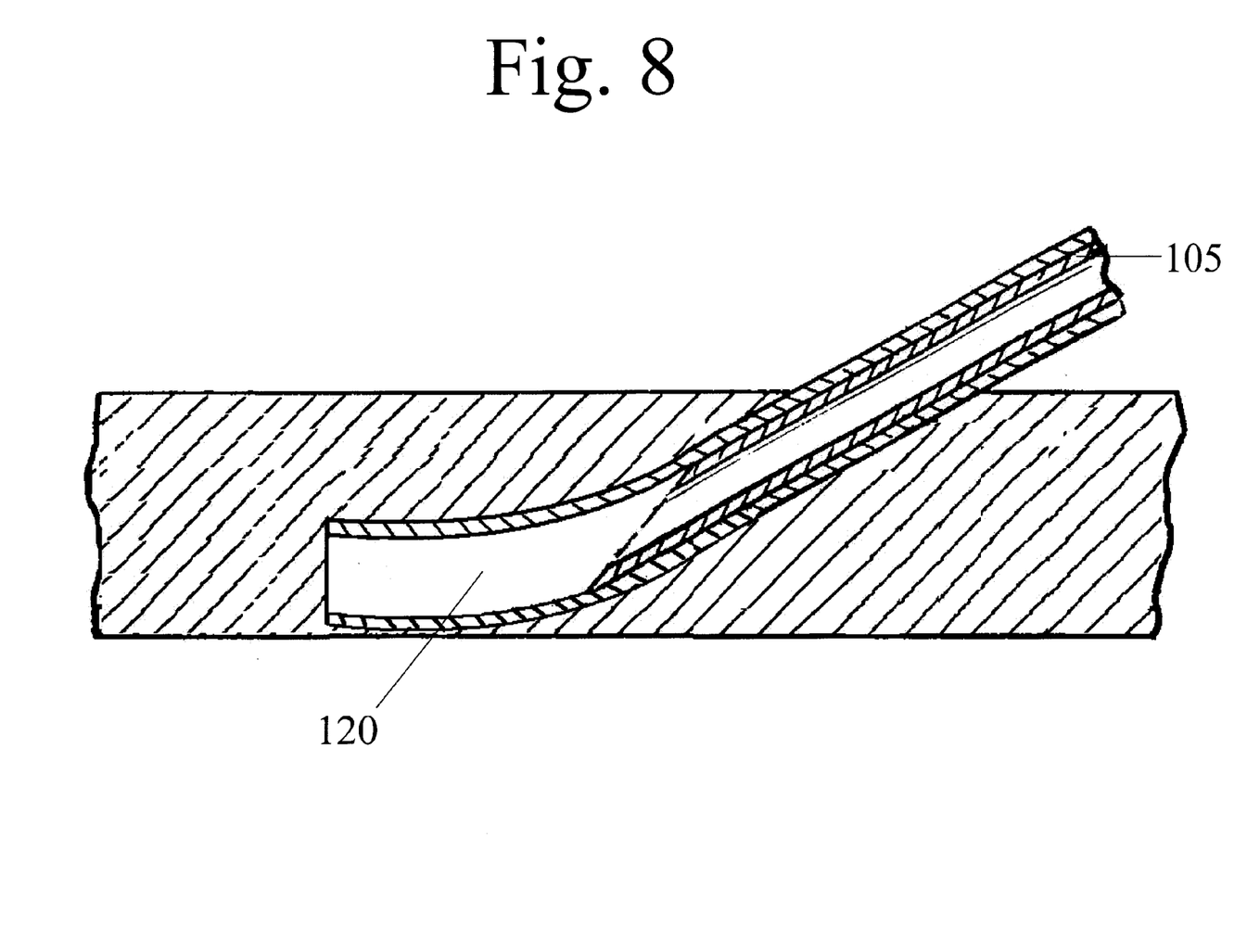
FIG. 8 illustrates an alternative method of radiation catheter placement.

In another embodiment, irradiation of neoplastic lesions can be accomplished using the catheter-based radiation delivery system. A needle is passed into a tumor under radiographic guidance as is commonly performed in current medical practice. A catheter-based radiation delivery system is then passed through the needle bore into the tumor as shown in FIG. 1 and the lesion is irradiated. The catheter can be alternatively passed into the tumor over a central needle, as shown in FIG. 8, or over a guide wire. The needle can be also used to inject agents into the tumor that potentiate the effects of radiation.

Regardless of the specifics of the embodiment, it should be appreciated that placement of the radiation delivery catheter at the target site can be performed in a variety of ways. For example, the catheter can be guided through the central bore of a needle device, as shown in FIG. 1. Alternatively, the catheter 120 can be advanced atop the outer wall of the needle device 105, as shown in FIG. 8. Finally, a guide wire can be placed at the target site through the central bore of a needle device. After removal of the needle, the catheter is then advanced to the target site over the outer surface of the guide wire.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method for the treatment of a pain complaint of a subject using a removable catheter-based source of ionizing radiation, comprising:

localizing a spinal nerve as it exits a spinal column of the subject, the localized spinal nerve being identified as a component of the pain complaint of the subject;

accessing the spinal nerve percutaneously through an internal bore of a cannula, a distal aspect of the cannula being positioned in proximity to the localized spinal nerve as the nerve exits the spinal column;

advancing a catheter through the bore of the cannula, a distal region of the catheter being in proximity to the localized spinal nerve as the nerve exits the spinal column, the catheter configured to deliver ionizing radiation; and delivering a desired dose of ionizing radiation to the localized spinal nerve, the spinal nerve being in proximity to an exit site of the nerve from the spinal column;

removing the catheter and the cannula after administration of the ionizing radiation dose.

2. A method for the treatment of a pain complaint of a subject as in claim 1, wherein the localized spinal nerve is accessed in proximity to a neural foramen thereof.

3. A method for the treatment of a pain complaint of a subject as in claim 1, further comprising inserting a guidewire through the internal bore of the cannula and delivering the catheter to the localized spinal nerve over the guidewire.

4. A method for the treatment of a pain complaint of a subject as in claim 1, wherein localizing the spinal nerve as a component of the pain complaint of the subject comprises:

injecting an anesthetic along a spinal nerve that innervates a suspected site of pain; and determining whether an alleviation of pain occurs in response to the anesthetic injection.

5. A method for the treatment of a pain complaint of a subject as in claim 1, wherein the ionizing radiation is at least one of a form of alpha radiation, beta radiation, or gamma radiation.

6. A method for the treatment of a pain complaint of a subject as in claim 1, wherein the catheter is coupled to a source of ionizing radiation.

7. A method for the treatment of a pain complaint of a subject as in claim 6, wherein the source of ionizing radiation is external to the radiation delivery catheter.

8. A method for the treatment of a pain complaint of a subject as in claim 6, wherein the source of ionizing radiation is internal to the radiation delivery catheter.

9. A method for the treatment of a pain complaint of a subject as in claim 1, wherein the catheter is at least partially formed of radioactive material.

10. A method for the treatment of a pain complaint of a subject as in claim 1, wherein the catheter is at least partially formed of shape memory alloy.

* * * * *